United States Patent [19]

Edamatsu et al.

[11] 4,156,231

[45] May 22, 1979

[54] AUTOMATED PATTERN INSPECTION SYSTEM

[75] Inventors: Kunihiko Edamatsu; Yasukazu Sano, both of Kawasaki, Japan

[73] Assignee: Fuji Electric Co. Ltd., Kawasaki, Japan

[21] Appl. No.: 925,394

[22] Filed: Jul. 17, 1978

[30] Foreign Application Priority Data

Jul. 18, 1977 [JP] Japan .................................. 52/85755

[51] Int. Cl.² ............................................. G06K 9/00
[52] U.S. Cl. .................... 340/146.3 AE; 340/146.3 H; 364/564
[58] Field of Search ............ 340/146.3 MA, 146.3 H, 340/146.3 AC, 146.3 AE; 364/463, 507, 515, 516, 517, 560, 561, 564, 562

[56] References Cited

U.S. PATENT DOCUMENTS

| | | | |
|---|---|---|---|
| 3,576,980 | 5/1971 | Doyle | 340/146.3 AC |
| 3,757,299 | 9/1973 | Perry | 340/146.3 AC |
| 3,980,870 | 9/1976 | Kawahara | 340/146.3 AC |
| 4,097,847 | 6/1978 | Forsen et al. | 340/146.3 AE |

*Primary Examiner*—Leo H. Boudreau
*Attorney, Agent, or Firm*—Spencer & Kaye

[57] ABSTRACT

An automated pattern inspection system comprising first means for measuring an area value of an object digitized pattern, second means for computing a first square value of a boundary length from the area value, third means for detecting a boundary of the object digitized pattern, fourth means for computing a second square value of a length of the boundary detected by the third means, fifth means for computing a subtraction value between the first square value from the second means and the second square value from the fourth means, and sixth means for comparing the subtraction value from the fifth means with a reference level, whereby a condition of defect in the pattern is evaluated. According to this invention, any defect in an object pattern, regardless of its size, can be detected with a high speed operation, since this system does not require a square root extraction process.

6 Claims, 10 Drawing Figures

AUTOMATED PATTERN INSPECTION SYSTEM

BACKGROUND OF THE INVENTION

1. Field of the Invention

The present invention relates to an automated pattern inspection system, and more particularly to an automated defective pattern inspection system for detecting and evaluating defects in a digitized image pattern such as circular, square and regular polygonal patterns by comparing a squared boundary length derived from a measured boundary length of the pattern with another squared boundary length obtained from a measured area of the same pattern.

2. Prior Art

A requirement exists for the detection and evaluation of defects in a digitized image pattern automatically and within a short period of time. For example, in the case of a character recognition system wherein the character recognition rate is improved by detecting and correcting the omission or ambiguity of a character pattern, or in the case of a printed circuit board or integrated circuit photomask, a small part of the image pattern of which is detected as a digitized pattern by means of an image sensor or television camera, there is a need to judge whether the digitized pattern is fatally defective or not.

Hitherto, there has been proposed an apparatus for eliminating and extracting a small defective portion in a pattern as in Japanese Patent Application No. 97122/71 (Japanese Unexamined Patent Application Publication No. 61030/73). In this pattern inspection apparatus, a portion having either one of two conditions of a digitized pattern is first expanded and thereafter compressed or first compressed and thereafter expanded in such a manner that a small portion (the defective portion) contained in the pattern is eliminated. After this elimination process, a pattern obtained by the elimination of the small portion is compared with the original pattern so as to extract the small portion in the original pattern. This apparatus has disadvantages in that there is the possibility that an irregular boundary of the object pattern caused by sampling errors when the pattern is sampled will be extracted as a defect and in that a large size filter is required in order to detect a relatively large defect thereby complicating the construction of the apparatus.

With the above in mind, the inventors have proposed a defect recognition apparatus in Japanese Patent Application No. 9558/76 (Japanese Unexamined Patent Application Publication No. 93248/77), based upon the principle that the total boundary length of a pattern is prolonged if the pattern has a defect therein. In this apparatus, a boundary length calculated from the actual area of the pattern is compared with a boundary length obtained by measuring the boundary itself in order to evaluate the size of a defect. In this prior art apparatus, picture elements of an image pattern along the boundary in the X or Y direction are detected so as to count the number of these picture elements, and at the same time picture elements along the boundary in both of the X and Y directions are detected so as to count the number of these picture elements. The boundary length of the image pattern is computed from these two count values and thereafter compared with a second boundary length calculated from the actual area of the pattern to judge whether or not the pattern contains a defect. According to this apparatus, not only a relatively small defect but also a relatively large defect can be recognized and in addition this recognition can be performed by a simple arrangement.

In this apparatus, however, it is necessary to perform square root operation in either of the above mentioned computations for the boundary lengths, and it takes an extremely long computing time to perform the square root operation. Accordingly, it takes an extremely long time to obtain these boundary lengths.

In other words, if substantially the same defect evaluation can be realized without the square root computation, the evaluation can be completed within a shortened computing time. This leads to a high speed defect inspection apparatus.

SUMMARY OF THE INVENTION

With the above in view, it is an object of this invention to provide an automated pattern inspection system wherein an object pattern is evaluated within a short time without the square root computation so as to solve the above described problems.

It is another object of this invention to provide an automated pattern inspection apparatus having substantially the same quality of the defect evaluation as in the prior art case where the square root computation is employed.

An automated pattern inspection system of this invention comprises first means for measuring an area value of an object digitized pattern, second means for computing a first square value of a boundary length from said area value, third means for detecting a boundary of said object digitized pattern, fourth means for computing a second square value of a length of said boundary detected by said third means, fifth means for computing a subtraction value between said first square value from said second means and said second square value from said fourth means, and sixth means for comparing said subtraction value from said fifth means with a reference level, whereby evaluating a condition of defect in said pattern.

With the above mentioned objects in mind, the following description, by way of nonlimiting embodiments of this invention, is given in conjunction with the following drawings.

DESCRIPTION OF PREFERRED EMBODIMENTS

Figure 1:
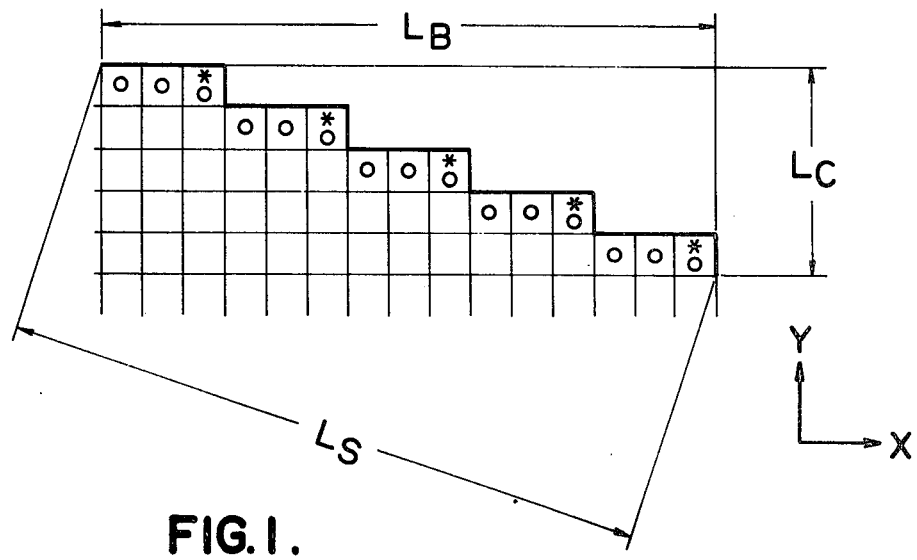
FIG. 1 is a diagram showing a part of a digitized image pattern.

FIG. 1 illustrates a part of a digitized image pattern or digital lattice of a pattern image in which an oblique straight boundary of the image pattern is composed of a number of fragmentary boundary sides, each of which has a number of picture elements having either one of two levels corresponding to the binary digit "0" or "1". Here, it is assumed that a mark ○ is allotted to a picture element having a boundary in either an X or Y direction and that a mark * is allotted to a picture element having a boundary in both of the X and Y directions. In addition, it is assumed that the number of picture elements having the mark ○ and contained in the five digitized boundary sides shown in FIG. 1 is represented by $L_B$, and the number of picture elements having the mark * and contained in the five digitized boundary sides shown in FIG. 1 is represented by $L_C$. These numbers $L_B$ and $L_C$ correspond to component lengths of the boundary length. In FIG. 1, the numbers $L_B$ and $L_C$ correspond to component lengths in the X and Y directions, respectively. In other words, by way of broader definition, the number $L_B$ corresponds to a longer component length of the two component lengths and the number $L_C$ corresponds to a shorter component length of the two component lengths, since the number $L_B$ includes picture elements having either of the marks ○ and *, while the number $L_C$ includes picture elements having both of the marks ○ and *.

The boundary length $L_S$ of the fragmentary boundary shown in FIG. 1 is defined by the component lengths $L_B$ and $L_C$ as follows;

$$L_S = \sqrt{L_B^2 + L_C^2} \tag{1}$$

With respect to an object pattern as a whole, its total boundary length L along the whole digitized boundary of that pattern is represented by the following equation (2).

$$L = \Sigma L_S = \Sigma_T \sqrt{L_B^2 + L_C^2} \tag{2}$$

This total boundary length L can be approximated by a hypotenuse of a right angle triangle having a base of $$\Sigma_{T} L_B$$

and a perpendicular of $$\Sigma_{T} L_C$$

as follows;

$$L \doteq \sqrt{(\Sigma_T L_B)^2 + (\Sigma_T L_C)^2} \tag{3}$$

The difference between the actual and approximated boundary lengths given by these equations (2) and (3) is sufficiently small if the boundary of a pattern has a number of picture elements, so that the approximation error due to this difference is negligible from a practical viewpoint. One example of this difference will be explained in the case of a fragmentary boundary sides forming a part of an image pattern shown in FIG. 2.

Figure 2:
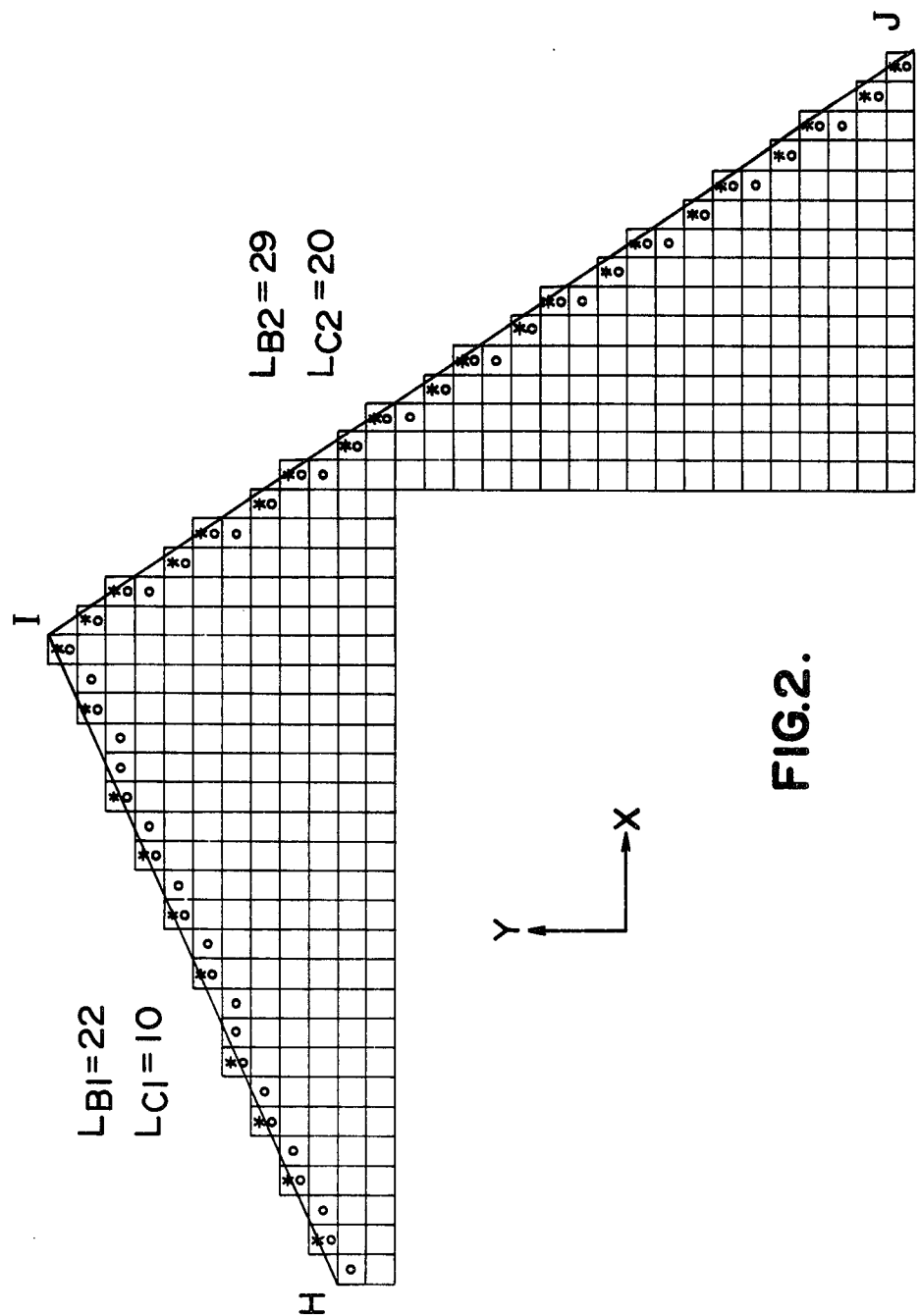
FIG. 2 is a diagram showing a part of another digitized image pattern.

In FIG. 2, there are illustrated two boundary sides, which are digitized as shown in FIG. 1. One side $\overline{HI}$ has the X direction length (larger component length) $L_{B1} = 22$ and the Y direction length (smaller component length) $L_{C1} = 10$. The other side $\overline{IJ}$ has the Y direction length (larger component length) $L_{B2} = 29$ and the X direction length (smaller component length) $L_{C2} = 20$.

Figure 3:
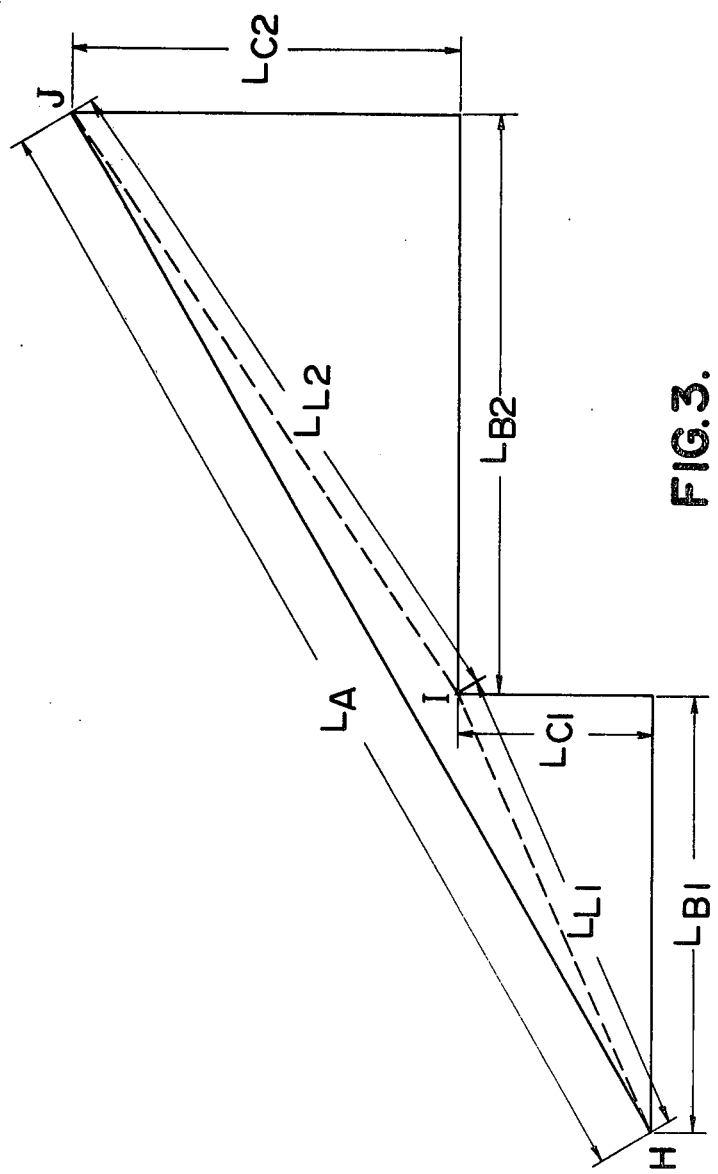
FIG. 3 is a diagram for explaining the process of calculating the boundary length of the part shown in FIG. 2.

These two sides $\overline{HI}$ and $\overline{IJ}$ have base and perpendicular projections, as illustrated in FIG. 3. In FIG. 3, one side $\overline{HI}$ having an inclination angle smaller than $\pi/4$ against the X axis has a base projection $L_{B1}$ and a perpendicular projection $L_{C1}$, while the other side $\overline{IJ}$ having an inclination angle larger than $\pi/4$ against the X axis has a base projection $L_{B2}$ and a perpendicular projection $L_{C2}$. Accordingly, the actual boundary length $L_L$ of these two boundary sides is given as follows;

$$L_L = L_{L1} + L_{L2}$$

$$L_L = \sqrt{(L_{B1})^2 + (L_{C1})^2} + \sqrt{(L_{B2})^2 + (L_{C2})^2}$$

$$L_L = 24.163 + 35.224$$

$$L_L = 59.387 \tag{4}$$

On the other hand, the approximated boundary length $L_A$ in this case is calculated by the following equation (5).

$$L_A = \sqrt{(L_{B1} + L_{B2})^2 + (L_{C1} + L_{C2})^2}$$

$$L_A = 59.169 \tag{5}$$

Therefore, this approximated boundary length $L_A$ has the following error $\epsilon$.

$$\epsilon = (L_L - L_A)/L_L \times 100 = 0.37[\%] \tag{6}$$

From the result of the above equation (6), it is understood that the approximated boundary length $L_A$ has only a negligible error and can be used as an amount representing the boundary length.

In embodiments of this invention which will be explained hereinafter, an approximated length thus obtained by equation (3) is used from a practical point of view. This, however, does not mean that means for calculating a boundary length in this invention is limited to means for performing equation (3).

Figure 4:
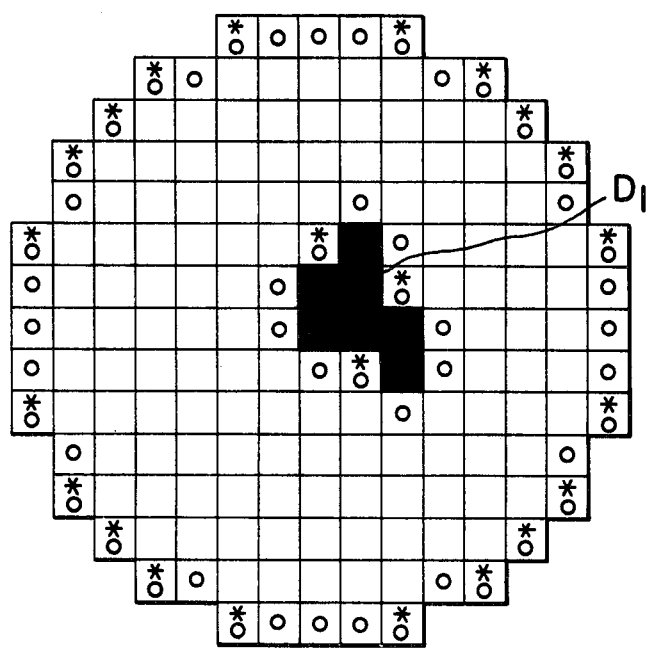
FIG. 4 is a diagram showing a digitized image pattern having a defect.

FIG. 4 illustrates a substantially circular digitized pattern having a defect $D_1$ composed of seven black picture elements. Here, a white picture element corresponds to a binary level "1" and a black picture element corresponds to a binary level "0", or vice versa. If there is no defect in this circular pattern, i.e., all of the picture elements in this pattern have the binary level "1", the amount S of the area of this circular pattern is obtained by counting the number of the picture elements having the binary level "1" and is equal to 177. The number $L_B$ of picture elements in contact with the boundary in either one of the X and Y directions or in both of the X and Y directions, i.e., the number of boundary picture elements in the X or Y direction having a mark ○ or * is equal to 40. Further, the number $L_C$ of picture elements in contact with the boundary in both of the X and Y directions, i.e., the number of boundary picture elements in the X and Y directions having only a mark * is equal to 20.

The square value of a boundary length $L_0$ calculated from the area value $S=177$ is given as follows;

$$L_0^2 = 4\pi S = 4 \times 3.14 \times 177 = 2223 \qquad (7).$$

On the other hand, the square value of a boundary length $L_1$ measured in accordance with the principle of equation (3) is given as follows;

$$L_1^2 = L_B^2 + L_C^2 = 40^2 + 20^2 = 2000 \qquad (8).$$

These equations (7) and (8) show that the squared boundary lengths $L_0^2$ and $L_1^2$ are approximately equal to each other. This relationship of $L_0^2 \doteq L_1^2$ means that there is no defect in the pattern. In this example, the circular pattern is quantized or digitized roughly for the convenience of its illustration, so that the order of approximation is not high. In an actual application, a pattern is divided into smaller sections, so that a higher correspondence can be expected. For example, in the case that a circular pattern is approximated by a regular octagon, the maximum error is expected to be about 2.5%.

On the other hand, in the case that there exists a defect $D_1$ in the circular pattern, as shown in FIG. 4, an additional boundary is formed around the defect $D_1$, so that the total boundary length is increased. The square value of a boundary length $L_{0D}$ derived from an area value $S_D = S - 7 = 170$ and the square value of a second boundary length $L_{1D}$ measured in accordance with the number of boundary picture elements are given as follows;

$$L_{0D}^2 = 4 \times 3.14 \times 170 = 2135 \qquad (9)$$

$$L_{1D}^2 = 51^2 + 23^2 = 3130 \qquad (10).$$

Obviously, the relationship of $L_{0D}^2 < L_{1D}^2$ is obtained in this case, so that the existence of the defect can be easily recognized in comparison with the former case where there is no defect and $L_0^2 \doteq L_1^2$ as shown in equations (7) and (8).

The inventors of this invention have found this principle and applied this principle to complete an automated pattern inspection system of this invention.

Figure 5:
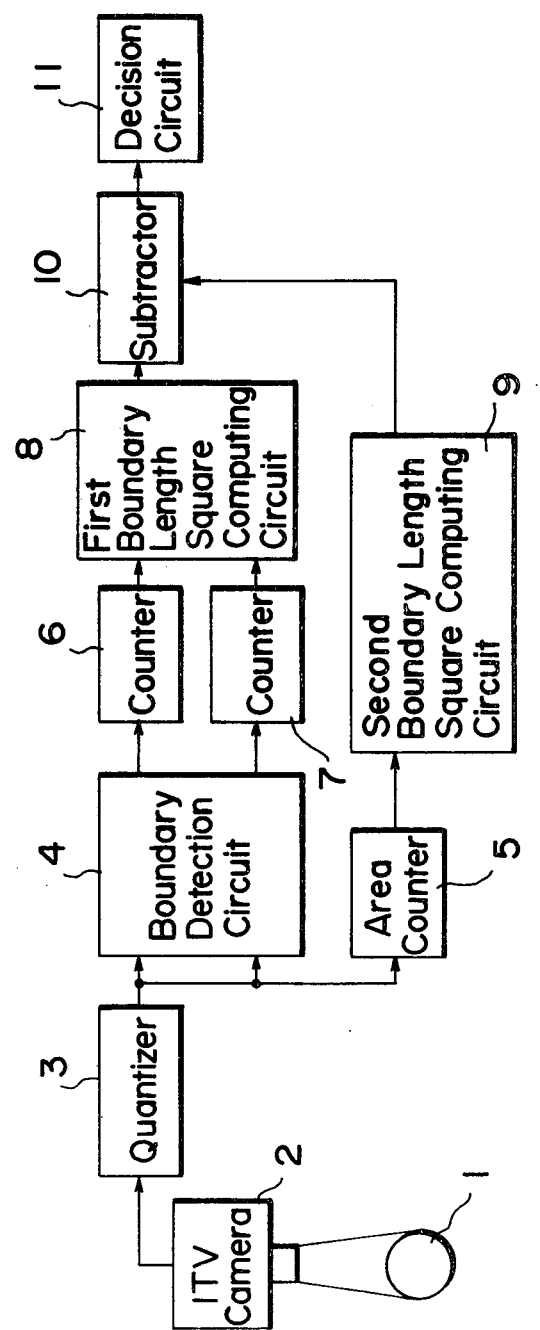
FIG. 5 is a block diagram showing one embodiment of an automated pattern inspection system according to this invention.

FIG. 5 shows one embodiment of an automated pattern inspection system according to this invention. In FIG. 5, a reference numeral 1 designates an object image pattern, for example, a circular pattern plate. The surface of this pattern 1 is scanned by a conventional industrial television camera 2 to produce an analog image signal or video signal. The analog image signal is applied to a quantizer 3 in which the analog image signal is first converted to a binary image signal with respect to a given defect detection threshold level and then sampled in comformity with the number of picture elements. For example, the view field of the television camera 2 is transformed to have $320 \times 240$ picture elements by the quantizer 3. The quantizer 3 may be formed by a conventional arrangement employing the fixed-type or floating-type thresholding principle. The sampled binary signal is applied serially to a boundary detection circuit 4 and an area counter 5. From this boundary detection circuit 4, a first boundary detection signal corresponding to a boundary picture element in the X or Y direction and a second boundary detection signal corresponding to a boundary picture element in the X and Y directions are derived and supplied to counters 6 and 7, respectively. The counter 6 counts the number $L_B$ of boundary picture elements in the X or Y direction and the counter 7 counts the number $L_C$ of boundary picture elements in X and Y directions. The area counter 5, which receives the binary sampled signal, counts the number thereof to compute the area value S of the digitized pattern corresponding to the object pattern 1.

Further, in FIG. 1, a counter output signal representing the number $L_B$ from the counter 6 and a counter output signal representing the number $L_C$ from the counter 7 are supplied to a first boundary length square computing circuit 8 in which an amount $L_B^2 + L_C^2$ is computed. This amount $L_B^2 + L_C^2$ is equal to a first squared boundary length $L_1^2$ measured in accordance with the principle of equation (3). A counter output signal representing the area value S is applied to a second boundary length square computing circuit 9 in which the area value S is multiplied by a constant factor $4\pi$ to obtain a product $4\pi S$. This product corresponds to a second squared boundary length $L_0^2$ calculated in accordance with equation (7).

A squared boundary length output signal from the first boundary length square computing circuit 8 and a squared boundary length output signal from the second boundary length square computing circuit 9 are applied to a subtractor 10 to obtain a difference $L_1^2 - L_0^2$. This difference signal is applied to a decision circuit 11 in which the difference $L_1^2 - L_0^2$ is compared with a predetermined threshold value to judge the size of a defect in accordance with the result of this comparison.

Figure 6:
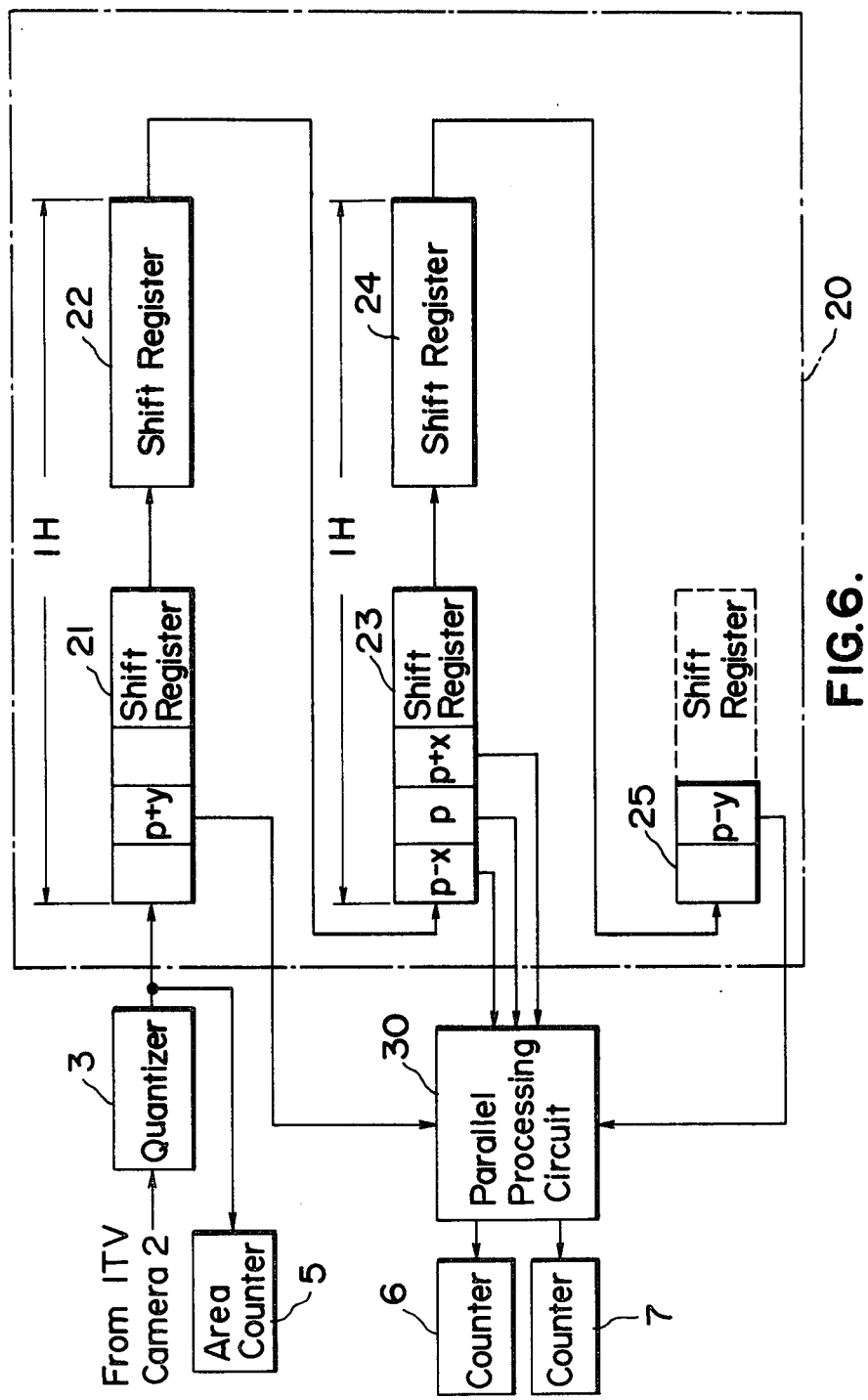
FIG. 6 is a block diagram showing one embodiment of a boundary detection circuit shown in FIG. 5.

FIG. 6 shows one embodiment of a boundary detection circuit 4 shown in FIG. 5. In this FIG. 6, the binary image signal derived from the quantizer 3 is sequentially applied to a two-dimensional local memory 20 and stored therein. The output signals from this memory 20 are applied to a parallel processing circuit 30, from which the above mentioned first and second boundary detection signals are obtained. The two-dimensional local memory 20 may be composed of two 1H shift registers (wherein 1H corresponds to one horizontal line period of the television camera 2) and a two-bit shift register which are connected in series. In the embodiment shown in FIG. 6, this memory 20 has a first eight-bit shift register 21, a first 320-bit shift register 22, a second eight-bit shift register 23, a second 320-bit shift register 24 and a two-bit shift register 25 which are connected in series in this sequence. The first and second eight-bit shift registers 21 and 23 and the two-bit shift register 25 have a serial input terminal and parallel output terminals, respectively. The first and second 320-bit registers 22 and 24 have a serial input terminal and a serial output terminal. The first eight-bit shift register 21 receives the binary image signal from the quantizer 3. The second bit output signal $P+y$ from the first eight-bit shift register 21, the first, second and third bit output signals $P-x$, $P$ and $P+x$ from the second eight-bit shift register 23 and the second bit output from the two-bit shift register 25 are applied to the succeeding parallel processing circuit 30.

Figure 7:
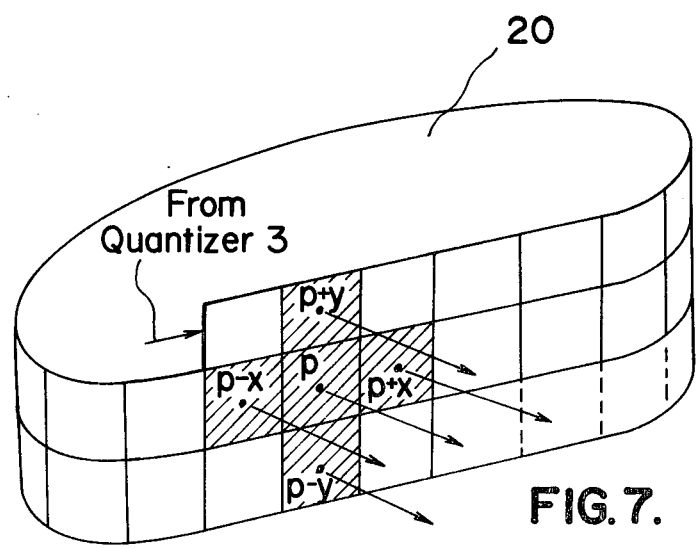
FIG. 7 is an explanatory diagram showing one embodiment of a two-dimensional local memory shown in FIG. 7.

In this embodiment, one horizontal line of the industrial television camera 2 corresponds to 328 picture elements, i.e., to 328 bits in these serial shift registers and these registers are driven by a clock signal, having a frequency of about 6 MHz, so that a binary image signal during one horizontal line period is contained in the first 1H shift register composed of the two shift registers 21 and 22 and subsequently shifted one bit by one bit to the second 1H shift register composed of the two shift registers 23 and 24. Then, if the second 1H shift register contains the binary image signal in full, the binary image signal is shifted one bit by one bit to the final two-bit shift register 25. Accordingly, the respective two register output signals P−y, and P, and P and P+y have one H time difference. The respective two register output signals P−x and P, and P and P+x have one bit time difference. The relationship of these five shift register output signals P+y, P−x, P, P+x and P−y is illustrated in FIG. 7 wherein one round of register sections forms the above mentioned 1H register. In this way, the two-dimensional local memory 20 forms a two-dimensional filter for extracting the image signal in a cross shaped fashion as shown in FIG. 7. In other words, the digitized pattern is scanned through the cross shaped filter to detect the boundary of the pattern.

Further, a commercially available high speed register like the integrated circuit SN 74164 of Texas Instruments may be used as the eight-bit shift registers 21 and 23 and the two-bit shift register 25, and the integrated circuit TMS 3409 of Texas Instruments may be used as the 320-bit shift registers 22 and 24. The final shift register stage 25 requires only two bits, so that any high speed shift register having at least two bits may be used.

Figure 8:
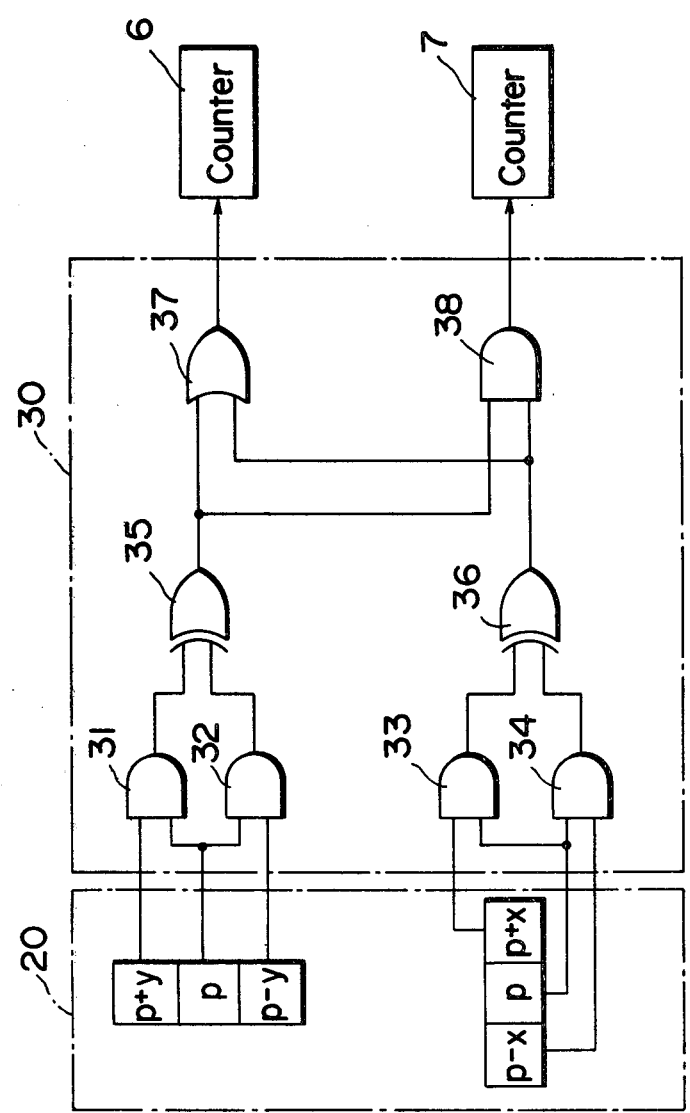
FIG. 8 is a block diagram showing one embodiment of a parallel processing circuit in the boundary detection circuit shown in FIG. 6.

An embodiment of the parallel processing circuit 30 is shown in FIG. 8. The parallel processing circuit 30 has a first AND gate 31 receiving the register output signals P+y and P, a second AND gate 32 receiving the register output signals P and P−y, a third AND gate 33 receiving the register output signals P and P+x and a fourth AND gate 34 receiving the register output signals P−x and P. The AND output signals from the AND gates 31 and 32 are applied to a first exclusive OR gate 35, and the AND output signals from the AND gates 33 and 34 are applied to a second exclusive OR gate 36. The exclusive OR output signals from the exclusive OR gates 35 and 36 are applied to an OR gate 37 and at the same time to a fifth AND gate 38. The OR output signal from the OR gate 37 is applied to the counter 6, and the AND output signal from the AND gate 38 is applied to the counter 7.

The first exclusive OR gate 35 produces the output signal "1" when the register output signals P+y and P−y have the different binary levels. In other words, if two picture elements adjacent to one picture element in the Y direction have the different binary levels, the exclusive OR gate 35 produces its exclusive OR output signal. Therefore, this exclusive OR gate 35 detects a boundary in the Y direction. On the other hand, the second exclusive OR gate 36 produces the output signal "1" when the register output signal P+x and P−x have the different binary levels. In other words, if two picture elements adjacent to the above mentioned one picture element in the X direction have the different binary levels, the exclusive OR gate 36 produces its exclusive OR output signal. Accordingly, this exclusive OR gate 36 detects a boundary in the X direction. As a result, the OR gate 37 produces the OR output signal representing the first boundary detection signal which is formed in the case that any boundary picture element (marked O or *) exists either in the X or Y direction. The AND gate 38 produces the AND output signal representing the second boundary detection signal which is formed in the case that any boundary picture element (marked only *) exists both in the X and Y directions.

As the original pattern is scanned by the industrial television camera 2, the binary image signal is derived sequentially from the quantizer 3 and then applied to the two-dimensional local memory 20. Consequently, the five binary signals filtered through the memory 20 in the above mentioned cross shaped manner are sequentially applied to the parallel processing circuit 30, as the original pattern 1 is scanned by the television camera 2. The first and second boundary detection signals produced by the parallel processing circuit 30 are applied to the counters 6 and 7, respectively, in which the number $L_B$ of boundary picture elements in the X or Y direction and the number $L_C$ of boundary picture elements in the X and Y directions, both with respect to the whole pattern 1, are obtained by counting the number of occurrences of the first and second boundary detection signals, respectively, regardless of the location and/or attitude or inclination of the original pattern 1 in the view field of the television camera 2.

Further, the counters 6 and 7 as well as the area counter 5 may be formed by any counter which is commercially available on the market, for example, the integrated circuit SN 74161 of Texas Instruments.

Figure 9:
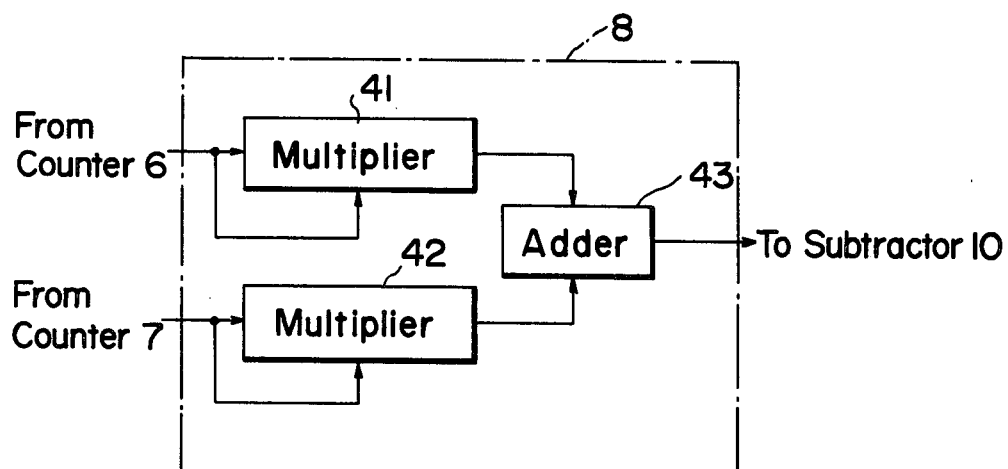
FIG. 9 is a block diagram showing one embodiment of a boundary length square computing circuit shown in FIG. 5.

One embodiment of the first boundary square circuit 8 shown in FIG. 5 is shown in FIG. 9, in which the counter output signal from the counter 6 indicating the number $L_B$ is applied to two input terminals of a first multiplier 41 and the counter output signal from the counter 7 indicating the number $L_C$ is applied to two input terminals of a second multiplier 42. Thus, these multipliers 41 and 42 function as a square-law multiplier and produce output signals corresponding to the square amounts $L_B^2$ and $L_C^2$, respectively, which are applied to an adder 43. The adder 43 produces an output signal which indicates the sum of the square amounts $L_B^2 + L_C^2$. Here, the multipliers 41 and 42 may be formed by a commercially available multiplier such as SN74LS275 of Texas Instruments, and the adder may be formed by a commercially available adder such as SN74283 of Texas Instruments.

Further, the second boundary length square computing circuit 9 shown in FIG. 5 can be also formed by a commercially available multiplier, for example the above mentioned SN74LS275. The subtractor 10 shown in FIG. 5 may be formed by a commercially available subtractor such as SN74283 of Texas Instruments.

Figure 10:
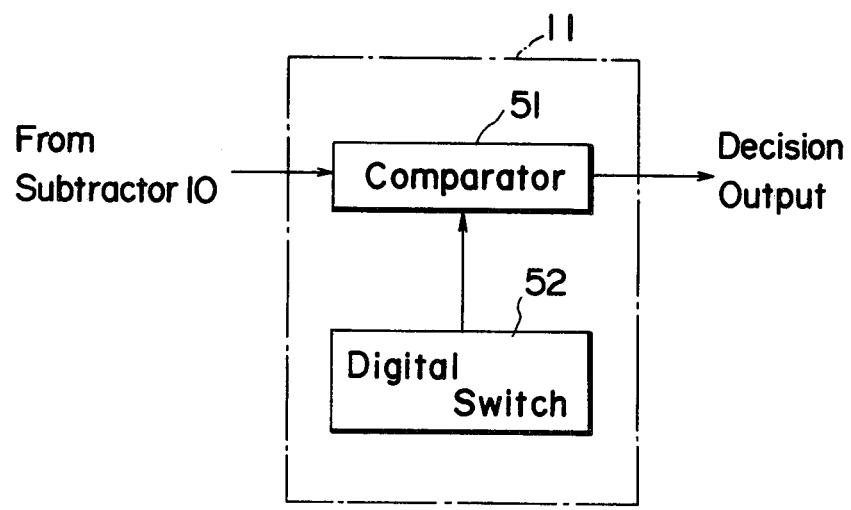
FIG. 10 is a block diagram showing one embodiment of a decision circuit shown in FIG. 5.

The circuit arrangement comprising the circuits 8 and 9 and the subtractor 10 can be practicably formed by a conventional micro-computer, unlike those composed with the hardware logic circuits as shown in FIGS. 9 and 10.

One embodiment of the decision circuit 11 shown in FIG. 5 is shown in FIG. 10 in which the subtraction result $L_1^2 - L_0^2 = (L_B^2 + L_C^2) - 4\pi S$ is applied to one input terminal of a comparator 51. The comparator 51 has another input terminal to which a reference level is applied from a reference level setter 52. The comparator produces a decision output signal in accordance with its comparison of the subtraction result with the reference level. The decision output signal indicates whether a defect exists in an object pattern or not. The comparator 51 may be formed by a commercially available comparator, for example, SN7485 of Texas Instruments. The reference level setter 52 may be formed by a conventional digital switch for setting levels of respective bits of the reference level in the binary form. This reference level is predetermined by computing, in advance, the subtraction results of a good or reference pattern and patterns having various kinds of typical defects including the most severe defect such as a dropout of one picture element by using a statistical method. This reference level is varied in accordance with the shape and size of a reference pattern. With this in view, the digital switch may preset a plurality of reference levels with which the detected subtraction result $L_1^2 - L_0^2$ is compared sequentially or in parallel with the plurality of reference levels so that the order or size of a defect in a pattern may be evaluated by judging a reference level which is the closest to the subtraction result.

Next, explanation will be made of a relationship of a defect evaluation in the case of this invention where the subtraction result $L_1^2 - L_0^2$ is used with a defect evaluation in the prior art case of Japanese Patent Application No. 9558/76 where the subtraction result $L_1 - L_0$ is used. If a difference value between the boundary lengths $L_1$ and $L_0$ is defined as $\Delta L$, then the following equation (11) is obtained.

$$L_1 - L_0 = \Delta L \quad (11)$$

A difference value between the squared boundary lengths $L_1^2$ and $L_0^2$ is expressed by using the relation of equation (11) as follows.

$$L_1^2 - L_0^2 = \Delta L (2L_0 + \Delta L) \quad (12)$$

If a defect is very small or is negligibly small, the following inequality (13) is obtained in so far as the number of picture elements dividing a pattern is large.

$$L_0 >> \Delta L \quad (13)$$

Therefore, equation (12) can be modified by using inequality (13) as follows.

$$L_1^2 - L_0^2 = 2L_0 \cdot \Delta L \quad (14)$$

In the case that the object pattern is a pattern of a uniform mass-produced product, the standard deviation with respect to the boundary length $L_0$ is negligible, so that the difference $L_1^2 - L_0^2$ in equation (14) is proportional to $\Delta L$, since the amount $2L_0$ is constant. In other words, the difference $L_1^2 - L_0^2$ is proportional to the difference $L_1 - L_0$. This means that the ability of defect evaluation in the case of $L_1^2 - L_0^2$ is equal to the ability of defect evaluation in the case of $L_1 - L_0$.

With respect to operation time, an experimental result has shown that it takes only about 5 msec to obtain the difference of the squared boundary lengths $L_1^2$ and $L_0^2$ in an automated pattern inspection system according to this invention, while it takes about 34 msec to obtain the difference of the boundary lengths $L_1$ and $L_0$ in the above mentioned prior art case, since the extraction of a square root $\sqrt{L_B^2 + L_C^2}$ or $\sqrt{4\pi S}$ is a time consuming process.

According to this invention, as described above, any defect in a pattern, regardless of its size, can be recognized with a high speed operation, since this invention does not require the square root extraction. The pattern inspection system according to this invention has substantially the same quality of defect evaluation as in the prior art case where the square root extractions $\sqrt{L_B^2 + L_C^2}$ and $\sqrt{4\pi S}$ are employed. Therefore, the pattern inspection system according to this invention can be applied advantageously and with a high speed operation to examine the quality of mass-produced product having a uniform shape and little standard deviation.

Further, while the object pattern in the above mentioned embodiment has a substantially circular shape, this invention is not limited to inspect only the circular shape and various kinds of patterns having a shape other than the circular shape may be an object pattern, the value of the area of which is measured by the counter in the digital form. In this case, a formula for deriving a boundary length from the measured area value is predetermined in accordance with the characteristic of the shape in a manner like the above described equation (7).

The invention has been described in detail with respect to preferred embodiments, and it will now be apparent from the foregoing to those skilled in the art that changes and modifications may be made without departing from the invention in its broader aspects, and it is the invention, therefore, in the appended claims to cover all such changes and modifications as fall within the true spirit of the invention.

What is claimed is:

1. An automated pattern inspection system comprising:
    first means for measuring an area value of an object digitized pattern,
    second means for computing a first square value of a boundary length from said area value,
    third means for detecting a boundary of said object digitized pattern,
    fourth means for computing a second square value of a length of said boundary detected by said third means,
    fifth means for computing a subtraction value between said first square value from said second means and said second square value from said fourth means, and
    sixth means for comparing said subtraction value from said fifth means with a reference level, whereby a condition of defect in said pattern is evaluated.

2. An automated pattern inspection system as claimed in claim 1, wherein said third means comprises seventh means for detecting first type picture elements forming boundary sides either in an X or Y direction, first counting means for counting the number of said first type picture elements, eighth means for detecting second type picture elements forming boundary sides both in the X and Y directions, and second counting means for counting the number of said second type picture elements, and said fourth means comprises a first square-law multiplier for computing a square value of said number of said first type picture elements, a second square-law multiplier for computing a square value of said number of said second type picture elements, and an adder for adding said square value from said first square-law multiplier to said square value from said second square-law multiplier, thereby deriving said second square value of said length of said boundary detected by said third means.

3. An automated pattern inspection system as claimed in claim 2, wherein said seventh means has first extracting means for extracting the binary contents in three picture elements located in succession in the Y direction, second extracting means for extracting the binary contents in three picture elements located in succession in the X direction, the middle picture element of which corresponds to the middle picture element of said three picture elements in the Y direction, first gate means receiving said binary contents from said first extracting means for detecting whether the side picture elements in said three successive picture elements in the Y direction have different binary contents, second gate means receiving said binary contents from said second extracting means for detecting whether the side picture elements in the X direction have different binary contents, an OR gate receiving output signals from said first and second extracting means for producing an OR output signal representing that said middle picture element forms a part of the boundary sides either in the X or Y direction, and a first AND gate receiving said output signals from said first and second extracting means for producing an AND output signal representing that said middle picture element forms a part of the boundary sides both in the X and Y directions, said OR output signal and said AND output signal being applied to said first and second counting means, respectively.

4. An automated pattern inspection system as claimed in claim 3, wherein each of said first and second gate means has a second AND gate receiving the binary contents from said middle and one side picture elements, a third AND gate receiving the binary contents from said middle and the other side picture elements, and an exclusive OR gate receiving AND output signals from said second and third AND gates.

5. An automated pattern inspection system as claimed in claim 3, wherein said first and second extracting means are formed by a two dimensional local memory having three successive lines of shift registers, the first and second shift registers of which have register elements corresponding respectively to one horizontal line period and the third shift register of which has at least two shift register elements, said three picture elements in the Y direction being derived from second shift register elements in said first, second and third shift registers and said three picture elements in the X direction being derived from first, second and third shift register elements in said second shift register.

6. An automated pattern inspection system as claimed in claim 4, wherein said first and second extracting means are formed by a two dimensional local memory having three successive lines of shift registers, the first and second shift registers of which have register elements corresponding respectively to one horizontal line period and the third shift register of which has at least two shift register elements, said three picture elements in the Y direction being derived from second shift register elements in said first, second and third shift registers and said three picture elements in the X direction being derived from first, second and third shift register elements in said second shift register.

* * * * *